United States Patent
Soong (10) Patent No.: US 12,116,363 B2
(45) Date of Patent: Oct. 15, 2024

(54) COMBINATIONS FOR IMMUNE-MODULATION IN CANCER TREATMENT

(71) Applicant: SENHWA BIOSCIENCES, INC., New Taipei (TW)

(72) Inventor: John Soong, San Diego, CA (US)

(73) Assignee: SENHWA BIOSCIENCES, INC., New Taipei (TW)

( * ) Notice: Subject to any disclaimer, the term of this patent is extended or adjusted under 35 U.S.C. 154(b) by 0 days.

(21) Appl. No.: 16/657,477

(22) Filed: Oct. 18, 2019

(65) Prior Publication Data
US 2020/0123153 A1  Apr. 23, 2020

Related U.S. Application Data (60) Provisional application No. 62/837,048, filed on Apr. 22, 2019, provisional application No. 62/747,822, filed on Oct. 19, 2018.

(51) Int. Cl.
| | |
|---|---|
| *C07D 471/04* | (2006.01) |
| *A61K 31/4375* | (2006.01) |
| *A61K 31/7068* | (2006.01) |
| *A61K 33/243* | (2019.01) |
| *A61K 45/06* | (2006.01) |
| *A61P 35/00* | (2006.01) |
| *A61P 35/04* | (2006.01) |
| *C07K 16/28* | (2006.01) |

(52) U.S. Cl.
CPC ............ *C07D 471/04* (2013.01); *A61P 35/00* (2018.01); *A61K 45/06* (2013.01)

(58) Field of Classification Search
CPC ........ C07D 471/04; A61P 35/00; A61P 35/04; A61K 45/06; A61K 31/4375; A61K 31/7068; A61K 33/243; A61K 2039/505; A61K 39/39558; A61K 31/4738; A61K 2300/00; C07K 16/2818
See application file for complete search history.

(56) References Cited

U.S. PATENT DOCUMENTS

| | | |
|---|---|---|
| 8,871,725 B2 | 10/2014 | Rodriguez et al. |
| 9,226,946 B2 | 1/2016 | Rodriguez et al. |
| 9,278,118 B2 | 3/2016 | Perea Rodriguez et al. |
| 9,993,551 B2 | 6/2018 | Lebwohl et al. |
| 11,344,620 B2 | 5/2022 | Lebwohl et al. |
| 2009/0130228 A1 | 5/2009 | Perea Rodriguez et al. |
| 2011/0065712 A1 | 3/2011 | Haddach et al. |
| 2011/0071115 A1 | 3/2011 | Haddach et al. |
| 2011/0071136 A1 | 3/2011 | Haddach et al. |
| 2015/0030700 A1 | 1/2015 | Rodriguez et al. |
| 2015/0111832 A1 | 4/2015 | Rodriguez et al. |
| 2017/0281624 A1 | 10/2017 | Peters et al. |
| 2017/0296659 A1 | 10/2017 | Lebwohl et al. |
| 2017/0304443 A1 | 10/2017 | Lebwohl et al. |

FOREIGN PATENT DOCUMENTS

| | | | |
|---|---|---|---|
| CN | 106963948 A | 7/2017 | |
| EP | 1911451 A1 | 4/2008 | |
| EP | 1997506 A1 | 12/2008 | |
| WO | 2008028168 A2 | 3/2008 | |
| WO | 2011011199 A1 | 1/2011 | |
| WO | 2016040882 A1 | 3/2016 | |
| WO | WO-2017070137 A1 * | 4/2017 | ......... C07K 16/2818 |
| WO | WO-2017197259 A1 * | 11/2017 | |

OTHER PUBLICATIONS

Siddiqui-Jain, A., "CK2 inhibitor CX-4945 suppresses DNA repair response triggered by DNA-targeted anticancer drugs and augments efficacy: mechanistic rationale for drug combination therapy." Molecular cancer therapeutics 11.4 (2012): 994-1005.*
Kim, H. M., "Overcoming cisplatin resistance through the combination treatment with CK2 inhibitor, CX-4945, in gastric cancer." Cancer Research 77.13_Supplement (2017): 1216-1216.*
Borad, M. J., (2017). Journal of Clinical Oncology, 35 (4), 294. doi: 10.1200/JCO.2017.35.4_suppl.294.*
NCT02128282 (Study of CX-4945 in Combination With Gemcitabine and Cisplatin for Frontline Treatment of Cholangiocarcinoma; May 1, 2014; p. 1-6.*
Chua, M.M.J., "CK2 in cancer: cellular and biochemical mechanisms and potential therapeutic target." Pharmaceuticals 10.1 (2017): 1-30.*
Koido, S., "Immunogenic modulation of cholangiocarcinoma cells by chemoimmunotherapy." Anticancer research 34.11 (2014): 6353-6361.*
International Search Report and Written Opinion in International Patent Application No. PCT/US2019/056994, dated Feb. 3, 2020, in 14 pages.
Extended European Search Report in EP Application No. 19874585.3 dated Jul. 4, 2022, in 16 pages.
Anonymous: "NCT02128282 Study of CX-4945 in Combination With Gemcitabine and Cisplatin for Frontline Treatment of Cholangiocarcinoma" Clinical Trials.gov archive, Sep. 5, 2018 (Sep. 5, 2018), v. 11, pp. 1-6, XP055933930.
Zakharia, Kais, et al. "Preclinical in vitro and in vivo evidence of an antitumor effect of CX-4945, a casein kinase II inhibitor, in Cholangiocarcinoma." Translational Oncology 12.1 (2019): 143-153.

(Continued)

*Primary Examiner* — John M Mauro
(74) *Attorney, Agent, or Firm* — DUANE MORRIS LLP (57) ABSTRACT

The present disclosure provides a method for treating a cancer or refractory cancer and/or inhibiting cancer metastasis, recurrence or progression in a subject or increasing the likelihood of survival over a relevant period in a subject diagnosed with a cancer, comprising administering to a subject a combination of an anti-cancer agent, a CK2 inhibitor and optionally an immune checkpoint inhibitor. The method of the present disclosure increases the number of T cells and activated T cells in the tumor microenvironment and thus can modulate immune in cancer therapy.

14 Claims, 8 Drawing Sheets
(7 of 8 Drawing Sheet(s) Filed in Color)

(56) References Cited

OTHER PUBLICATIONS

D'Amore, Claudio, et al. "Role of CK2 inhibitor CX-4945 in anti-cancer combination therapy—potential clinical relevance." Cellular Oncology 43.6 (2020): 1003-1016.
Jul. 7, 2023 Communication pursuant to Article 94(3) EPC issued by the European Patent Office for European Patent Application No. 19874585.3.
Valle, Juan et al., "Cediranib or placebo in combination with cisplatin and gemcitabine chemotherapy for patients with advanced biliary tract cancer (ABC-03): a randomised phase 2 trial." The Lancet Oncology, Aug. 1, 2015, 12 pages.
Vogel, Arndt et al., "PICCA study: panitumumab in combination with cisplatin/gemcitabine chemotherapy in KRAS wild-type patients with biliary cancer—a randomised biomarker-driven clinical phase II AIO study." European Journal of Cancer, vol. 92, Mar. 1, 2028, 9 pages.
Katsuyuki, M. et al., "11 The Casein Kinase II Inhibitor CX-4945 Has an Additive Effect With Gemcitabine and Cisplatin on Cholangiocarcinoma Xenografts." Gastroenterology, vol. 150, No. 4, Apr. 2016, 1 page.
Chong, Dawn Q. et al., "The landscape of targeted therapies for cholangiocarcinoma: current status and emerging targets." Oncotarget, vol. 7, No. 29, Jul. 19, 2016, 18 pages.
Apr. 14, 2023 Office Action and Search Report issued by the Russian Patent and Trademark Office for Russian Patent Application No. 2021127441. [English translation included.].
Sep. 12, 2023 Notice of Reasons for Refusal issued by the Japanese Patent and Trademark Office for Japanese Patent Application No. 2021-547036. [English translation included.].
Miyabe, K., et al. "The Casein Kinase II Inhibitor CX-4945 Has an Additive Effect With Gemcitabine and Cisplatin on Cholangiocarcinoma Xenografts", Gastroenterology, Apr. 2016, vol. 150, No. 4 (p. S4).
D.A. Kharkevich, The Pharmacology, 10th Edition, M.: GEOTAR-Media, 2010, Chapter 31, pp. 825-848, machine translation provided.
Hargadon K. M., Johnson C. E., Williams C. J., Immune checkpoint blockade therapy for cancer: An overview of FDA-approved immune checkpoint inhibitors // International Immunopharmacology, Sep. 2018, vol. 62, pp. 29-39.
V.G.Belikov, The Pharmaceutical Chemistry, M., General Pharmaceutical Chemistry, Second edition, published by Vysshaya Shkola, 1993, pp. 43-47, machine translation provided.
D.A. Kharkevich, The Pharmacology Manual—9th Edition as amended and revised—M.: GEOTAR-Media, 2006. pp. 66-67 and 45-50, machine translation provided.
M.D.Mashkovsky. The Medicaments, 14th Edition, vol. 1, Moscow, New Wave LLC Publisher S.B. Divov, 2002, pp. 8-9, machine translation provided.
Second Office Action in Russian Counterpart Application No. 2021114145, dated May 29, 2024, in 13 pages; Machine translation provided.

\* cited by examiner

COMBINATIONS FOR IMMUNE-MODULATION IN CANCER TREATMENT

Cross-Reference to Related Applications

This application claims the benefit of priority to U.S. Provisional Patent Application Ser. No. 62/837,048, filed Apr. 22, 2019, and U.S. Provisional Patent Application Ser. No. 62/747,822, filed Oct. 19, 2018, each of which are incorporated by reference herein in their entireties.

FIELD OF THE INVENTION

This invention relates to a field of cancer treatment. Particularly, the invention provides a method of treating a cancer using a combination of a chemotherapeutic agent, a CK2 inhibitor and an immune checkpoint inhibitor.

BACKGROUND OF THE INVENTION

Protein kinase CK2 is up-regulated in many human cancers, and thus has been considered as a target for cancer therapy (Chua et al., Pharmaceuticals 2017, 10, 18). CK2 inhibitors is shown to inhibit cell proliferation and can be used for treating neoplastic disorder such as breast cancer, prostate cancer, pancreatic cancer, lung cancer, hematopoietic cancer, colorectal cancer, skin cancer, and ovarian cancers (Chua et al., U.S. Pat. No. 9,062,043 B2). However, CK2 inhibitor alone may only have a moderate anti-cancer effect for certain cancer types.

Multiple series of CK2 inhibitors have been studied for their activities in inhibiting cell growth alone as well as combination with other anti-proliferation agents (U.S. Pat. Nos. 9,062,043B2; 7,956,064B2; publication WO 2010080170 A1 and WO 2011011199 A1). Combining CK2 inhibitors with an anti-cancer agent that prohibits cell growth such as alkylating agents, anti-metabolite, vinca alkaloid, taxane, topoisomerase inhibitors, anti-tumor antibiotics, and tyrosine kinase inhibitors to treat or ameliorate a neoplastic disorder has been disclosed in WO 2010080170 A1. Additionally, WO 2010008170 A1 also discloses combining CK2 inhibitors with immunosuppressive macrolide to treat a neoplastic disorder.

Certain CK2 inhibitors are also shown to combine with inhibitors to molecules that are essential in cell growth pathway such as AKT inhibitors, HDAC inhibitors, HSP90 inhibitors, mTOR inhibitors, PBK/niTGR inhibitors, PDK inhibitors, and antibody targeting tumor/cancer antigen to treat or ameliorating neoplastic disorders and/or inflammatory, autoimmune, or infectious disorders (WO 2011011199 A1).

However, there is a need to identify new compounds that are capable of enhancing immune responses to tumor cells.

SUMMARY OF THE INVENTION

In one aspect, the present disclosure provides a method for treating a cancer or refractory cancer and/or inhibiting cancer metastasis, recurrence or progression in a subject or increasing the likelihood of survival over a relevant period in a subject diagnosed with a cancer, comprising administering to a subject a combination of an anti-cancer agent, a CK2 inhibitor and optionally an immune checkpoint inhibitor.

In one embodiment, the anti-cancer agents are (i) anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene citrate and selective estrogen receptor modulators (SERDs) such as fulvestrant; (ii) aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors, such as cobimetinib; (v) lipid kinase inhibitors, such as taselisib; (vi) antisense oligonucleotides, particularly those which inhibit expression of genes in signaling pathways implicated in aberrant cell proliferation, for example, PKC-alpha, Raf and H-Ras, such as oblimersen; (vii) ribozymes such as VEGF expression inhibitors and HER2 expression inhibitors; (viii) vaccines such as gene therapy vaccines; topoisomerase 1 inhibitors; (ix) anti-angiogenic agents such as bevacizumab; and pharmaceutically acceptable salts, acids and derivatives of any of the above. In another embodiment, the anti-cancer agents are therapeutic antibodies such as alemtuzumab, bevacizumab; cetuximab; panitumumab, rituximab, pertuzumab, trastuzumab, trastuzumab, emtansine, and tositumomab.

In a further embodiment, the anti-cancer agent is chemotherapeutic agents including but not limited to cisplatin, gemcitabine, carboplatin, methotrexate, vincristine, adriamycin, bleomycin, hydroxyurea, salinosporamide A, bortezomib, PS-519, omuralide, cyclophosphamide, ifosfamide, 5-fluorouracil, vinblastine, docetaxel, doxorubicin, and paclitaxel.

In some embodiments of the present invention, the CK2 inhibitor is a compound having a structure of Formula I, or a pharmaceutically acceptable salt or ester thereof, Formula I wherein:
each $Z^1$, $Z^2$, $Z^3$, and $Z^4$ is N or $CR^3$;
each of $Z^5$, $Z^6$, $Z^7$ and $Z^8$ is N or $CR^6$;
none, one or two of $Z^1$-$Z^4$ are N and none, one or two of $Z^5$-$Z^8$ are N, and at least one of $Z^1$-$Z^4$ and $Z^5$-$Z^8$ is a nitrogen atom;
each $R^3$ and each $R^6$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or
each $R^6$ is independently halo, OR, $NR_2$, NROR, $NRNR_2$, SR, SOR, $SO_2R$, $SO_2NR_2$, $NRSO_2R$, $NRCONR_2$, NRCOOR, NRCOR, CN, OC(O)R, COR, $NO_2$, or a polar substituent selected from a carboxylic acid, a carboxylate salt, an ester, a carboxamide, a tetrazole, or a carboxy bioisostere selected the group consisting of and each $R^3$ is independently halo, OR, $NR_2$, NROR, $NRNR_2$, SR, SOR, $SO_2R$, $SO_2NR_2$, $NRSO_2R$, $NRCONR_2$, NRCOOR, NRCOR, CN, OC(O)R, COR, polar substituent as defined above, or $NO_2$, and at least one $R^3$ is a polar substituent;

wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, NR'COOR', NR'COR', CN, COOR', $CONR'_2$, OC(O)R', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S;

$R^4$ is H or an optionally substituted member selected from the group consisting of C1-C6 alkyl, C2-C6 heteroalkyl, and C1-C6 acyl;

each $R^5$ is an optionally substituted member selected from the group consisting of C1-10 alkyl, C2-10 alkenyl, C2-10 heteroalkyl, C3-8 carbocyclic ring, and C3-8 heterocyclic ring optionally fused to an additional optionally substituted carbocyclic or heterocyclic ring; or $R^5$ is a C1-10 alkyl, C2-10 alkenyl, or C2-10 heteroalkyl substituted with an optionally substituted C3-8 carbocyclic ring or C3-8 heterocyclic ring; and in each —$NR^4R^5$, $R^4$ and $R^5$ together with N may form an optionally substituted 3-8 membered ring, which may optionally contain an additional heteroatom selected from N, O and S as a ring member;

provided that when —$NR^4R^5$ in Formula (I) is —NH Φ, where Φ is optionally substituted phenyl:
if all of $Z^5$-$Z^8$ are CH or one of $Z^5$-$Z^8$ is N, at least one of $Z^1$-$Z^4$ is $CR^3$ and at least one $R^3$ must be a non-hydrogen substituent; or
if each $R^3$ is H, then Φ must be substituted;

wherein each $R^7$ is independently H or an optionally substituted member selected from the group consisting of C1-10 alkyl, C2-10 alkenyl, C2-10 heteroalkyl, C3-8 carbocyclic ring, and C3-8 heterocyclic ring optionally fused to an additional optionally substituted carbocyclic or heterocyclic ring; or $R^7$ is a C1-10 alkyl, C2-10 alkenyl, or C2-10 heteroalkyl substituted with an optionally substituted C3-8 carbocyclic ring or C3-8 heterocyclic ring.

In certain preferred embodiments of the present invention, the CK2 inhibitor is CX-4945.

In one embodiment, the immunotherapeutic agent is an immune checkpoint inhibitor. In some embodiments of the present invention, the immune checkpoint inhibitor is an antagonist of PD-1 or an antagonist of CTLA-4. In some embodiments, the immune checkpoint inhibitor is CTLA-4, PDL-1 or PD-1 antibodies. In some embodiments, the PD-1 or CTLA-4 inhibitors include without limitation humanized antibodies blocking human PD-1 such as lambrolizumab (anti-PD-1 Ab, trade name Keytruda) or pidilizumab (anti-PD-1 Ab), nivolumab (anti-PD-1 Ab, trade name Opdivo), ticilimumab (anti-CTLA-4 Ab), and ipilimumab (anti-CTLA-4 Ab).

In one embodiment, the administration results in immunological memory to said cancer. In one embodiment, the administration increases the number of T cells and activated T cells in the tumor microenvironment.

In one embodiment, the combination of an anticancer agent and a CK2 inhibitor can be administered concurrently, sequentially, intermittently or periodically.

Suitable treatment protocols for treating a subject having cancer or inhibiting cancer metastasis, recurrence or progression in a subject include, for example, administering at least one administration cycle.

In one embodiment, the method comprises at least one administration cycle, wherein the cycle is a period of eight weeks or less. In a further embodiment, the cycle is a period of four weeks.

In one embodiment, the administration cycle comprises administering to the subject one or more first treatments (e.g. induction therapy, such as a combination of anticancer agent and CK2 inhibitor) in an amount and regimen sufficient to achieve a response (partial or complete response).

In one embodiment, the administration cycle comprises administering CK2 inhibitor in every day and an anticancer agent once a week. In a further administration, the administration cycle further comprises administrating an immune checkpoint inhibitor twice a week.

In one embodiment, the chemotherapeutic agent, a CK2 inhibitor and optionally an immune checkpoint inhibitor are in synergistically effective amounts.

In one embodiment, the chemotherapeutic agent, a CK2 inhibitor and optionally an immune checkpoint inhibitor are administered at a dose effective to increase immunological response against the cancer in the subject.

In some embodiments, the CK2 inhibitor is daily administered in a dose in the range from about 25 mg per kg of subject weight (about 25 mg/kg) to about 2,000 mg/kg. In some embodiments, the daily dose is in the range of about 50 mg/kg to about 200 mg/kg. In some embodiments, the CK2 inhibitor is administered twice a day.

In some embodiments, the anticancer agent is administered in a dose in the range from about 1 mg per kg of subject weight (about 1 mg/kg) to about 20 mg/kg. In some embodiments, the dose is in the range of about 5 mg/kg to about 10 mg/kg.

In some embodiments, the immune checkpoint inhibitor is administered in a dose in the range from about 1 mg per kg of subject weight (about 1 mg/kg) to about 20 mg/kg. In some embodiments, the dose is in the range of about 8 mg/kg to about 15 mg/kg.

In some embodiments, the cancer includes, but is not limited to, skin cancer (such as melanoma and basal cell carcinoma), glioblastoma, liver cancer (such as hepatocellular carcinoma), colorectal carcinoma, glioblastoma, gastric cancer, colorectal cancer, esophageal cancer, lung cancer (such as non-small cell lung cancer (NSCLC) and small cell lung cancer), pancreatic cancer, renal cell carcinoma, benign prostate hyperplasia, prostate cancer, ovarian cancer, melanoma, breast cancer, chronic lymphocytic leukemia (CLL), Merkel cell carcinoma, Non-Hodgkin lymphoma, acute myeloid leukemia (AML), gallbladder cancer, cholangiocarcinoma, urinary bladder cancer, and uterine cancer.

According to the present invention, the subject may also be additionally administered with a CAR-T therapy.

In some embodiments, administration of therapeutic effective doses of combinational treatment decreases an expression of IL-6 mRNA or protein in a subject.

In some embodiments, administration of therapeutic effective doses of combinational treatment increases the immunological response of a subject against tumor. In some embodiments, the increased immunological response can be measured as high T cell number or activity in tumor microenvironment, lower MDSC systemically or in tumor microenvironment, or lower TAM in tumor microenvironment in a treated subject.

BRIEF DESCRIPTION OF THE DRAWING

The patent of application file contains at least one drawing executed in color. Copies of this patent or patent application publication with color drawing(s) will be provided by the Office upon request and payment of the necessary fees.

DETAILED DESCRIPTION OF THE INVENTION

It is to be understood that the terminology used herein is for the purpose of describing particular embodiments only and is not intended to be limiting.

Unless defined otherwise, all technical and scientific terms used herein have the same meaning as commonly understood by one of ordinary skill in the art to which the invention pertains. Generally, the nomenclature used herein and the experiment methods, which will be described below, are those well-known and commonly employed in the art.

As used herein, the terms "a" and "an" and "the" and similar references used in the context can be construed to cover both the singular and the plural.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the present application. Generally the term "about", as used herein when referring to a measurable value such as an amount of weight, time, dose, etc. is meant to encompass in one example variations of ±15% or ±10%, in another example ±5%, in another example ±1%, and in yet another example ±0.1% from the specified amount, as such variations are appropriate to perform the disclosed method.

As used herein, the term "therapeutically effective amount" refers to that amount which, when administered to an animal for treating a disease, is sufficient to effect such treatment for the disease, disorder, or condition.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms.

As used herein, "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

"Salts" include derivatives of an active agent, wherein the active agent is modified by making acid or base addition salts thereof. Preferably, the salts are pharmaceutically acceptable salts. Such salts include, but are not limited to, pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Base addition salts include but are not limited to, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e. g., lysine and arginine dicyclohexylamine and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Standard methods for the preparation of pharmaceutically acceptable salts and their formulations are well known in the art, and are disclosed in various references, including for example, "Remington: The Science and Practice of Pharmacy", A. Gennaro, ed., 20th edition, Lippincott, Williams & Wilkins, Philadelphia, PA.

As used herein, the term "synergistically effective" means that the combined effect of two or more therapeutic agents when used in combination is greater than their additive effects when used individually.

As used herein, the term "subject," "individual" or "patient" is used interchangeably herein, and refers to a vertebrate, preferably a mammal, more preferably a human.

As used herein, the term "immunotherapeutic agent" refers to chemicals and biologics which modulate a person's immune response to impart desirable therapeutic effect.

As used herein, the term "immune-suppressive cancer" or "immunosuppressive cancer" is a cancer associated with immunosuppressive characteristics systemically or in the tumor microenvironment in a subject. The immunosuppressive characteristics comprises any one of the followings: high regulatory T cells, high myeloid-derived suppressor cells (MDSC), high tumor associated macrophages (TAM), low presence or activity of CD4 or CD8 T cells, and low activity of antigen presentation cells (APC).

A tumor microenvironment is the cellular environment in which the tumor exists, comprising the surrounding blood vessels, hematopoietic precursors, immune cells, fibroblasts, extracellular matrix, and signaling molecules. The immune cells comprise lymphocytes and other hematopoietic cells that are pertinent to immune function (e.g. antigen presenting cells, macrophages, neutrophils, NK cells, monocytes, and myeloid-derived suppressor cells). The signaling molecules comprise cytokines, chemokines, growth factors and other soluble proteins that function in influencing the cellular activity and composition.

CK2 inhibitors have been shown to act synergistically with immune checkpoint modulators (ICM) such as an anti-PD1 antibody or an anti-Cytotoxic T Lymphocyte-associated Antigen 4 (CTLA-4) antibody. Both PD-1 and CTLA4 are known to suppress the costimulatory signaling that are essential for T cell activation. However, such CK2 inhibitors do not have effective tumor growth inhibition (TGI) properties when utilized alone (WO 2017/070137 A1). Additionally, a series of CK2 inhibitors, namely BMS-211, BMS-699, and BMS-595, were shown to decrease negative regulator of tumor-specific immune response, polymorphonuclear MDSC (PMN-MDSC) and tumor-associated macrophages (TAM), which likely to contribute to their synergistic effect with immune checkpoint inhibitors (Hashimoto et al., Cancer Res 78: 5644-5655).

The fact that merely antagonizing suppressive signaling molecules on T cells such as PD-1 or CTLA-4 is insufficient in controlling tumor growth through tumor-specific cytotoxic activity of T cells indicates that additional immune components in the tumor microenvironment may contribute to immune-suppressive mechanism that helps tumor evade T-cell mediated killing.

Accordingly, the present disclosure provides a method for treating a cancer or refractory cancer and/or inhibiting cancer metastasis, recurrence or progression in a subject or increasing the likelihood of survival over a relevant period in a subject diagnosed with a cancer, comprising administering to a subject a combination of an anti-cancer agent, a CK2 inhibitor and optionally an immune checkpoint inhibitor.

An anti-cancer agent used in the present disclosure may be a chemotherapeutic agent. Chemotherapeutic agents include conventional chemotherapeutic reagents such as alkylating agents, anti-metabolites, plant alkaloids, antibiotics, and miscellaneous compounds e.g., cis-platinum, CDDP, methotrexate, vincristine, adriamycin, bleomycin, and hydroxyurea. Chemotherapeutic drugs also include proteasome inhibitors such as salinosporamides (e.g., Salinosporamide A), bortezomib, PS-519, and omuralide. The most commonly used types of anticancer agents include: DNA-alkylating agents (e.g., cyclophosphamide, ifosfamide), antimetabolites (e.g., methotrexate, a folate antagonist, and 5-fluorouracil, a pyrimidine antagonist), microtubule disruptors (e.g., vincristine, vinblastine, paclitaxel), DNA intercalators (e.g., doxorubicin, daunomycin, cisplatin), and hormone therapy (e.g., tamoxifen, flutamide). Other platinum coordination complexes that have been evaluated in clinical trials include carboplatin, tetraplatin, ormiplatin, iproplatin and oxaliplatin (see Kelland, *Crit. Rev. Oncol. Hematol*, 15: 191-219 (1993)).

Alkylating agents include (a) alkylating-like platinum-based chemotherapeutic agents such as cisplatin, carboplatin, nedaplatin, oxaliplatin, satraplatin, and (SP-4-3)-(cis)-amminedichloro-[2-methylpyridine] platinum(II); (b) alkyl sulfonates such as busulfan; (c) ethyleneimine and methylmelamine derivatives such as altretamine and thiotepa; (d) nitrogen mustards such as chlorambucil, cyclophosphamide, estramustine, ifosfamide, mechlorethamine, trofosamide, prednimustine, melphalan, and uramustine; (e) nitrosoureas such as carmustine, lomustine, fotemustine, nimustine, ranimustine and streptozocin; (f) triazenes and imidazotetrazines such as dacarbazine, procarbazine, temozolamide, and temozolomide.

According to certain embodiments of the present invention, the chemotherapeutic agent may be selected from the group consisting of cisplatin, methotrexate, vincristine, adriamycin, bleomycin, hydroxyurea, salinosporamide A, bortezomib, PS-519, omuralide, cyclophosphamide, ifosfamide, methotrexate, 5-fluorouracil, vinblastine, and paclitaxel.

CK2 inhibitors can provide anti-cancer and anti-inflammatory potential. CK2 inhibitors are commonly classified into three categories: (1) inhibitors that target the regulatory subunit of CK2 (e.g., genetically selected peptide aptamers); (2) inhibitors of the catalytic activity of CK2 (e.g., quinobene, TBB, DMAT, IQA); and (3) disruptors of CK2 holoenzymes, which are often molecules binding to the CK2 subunit interface and inhibit the high affinity interaction of its subunits. The CK2 inhibitors of each class can be any type of molecule, such as a, small molecules, functional nucleic acids, antibodies, or peptide mimetics, etc.

CK2 catalytic subunits possess a constitutive activity. However, in eukaryotic cells the CK2β subunits are not only the central components of the tetrameric CK2 complex, but are also responsible for the recruitment of CK2 substrates. Thus, the dynamic interaction of the CK2 subunits observed in living cells can have a key role in CK2 signaling pathways. Drugs that specifically target this interaction are less likely to have side effects than drugs that act as general inhibitors of CK2 catalytic activity.

CK2 inhibitors consist of a diverse array of chemicals, including flavonoids (e.g. apigenin), derivatives of hydroxyantraquinones/xantenones (e.g., emodin), derivatives of hydroxycoumarines (e.g., DBC), derivatives of tetrabromotriazole/imidazole (e.g., DRB, TBB, DMAT, TBCA, TBBz), and derivatives of indoloquinazolines (e.g., IQA).

In certain embodiments, the CK2 inhibitors are the compounds represented by Formula I as described herein. According to certain embodiments of the present invention, the CK2 inhibitor may be selected from the group consisting of 4,5,6,7-tetrabromobenzotriazole (TBB), Quinalizarin, hematein, tetrabromocinnamic acid (TBCA), CIGB-300, CX-4945, 5,6-dichloro-1-beta-D-ribofuranosylbenzimidazole (DRB), apigenin, 2-Dimethylamino-4,5,6,7-tetrabromo-1H-benzimidazole (DMAT), emodin, 5-oxo-5,6-dihydro-indolo(1,2-a)quinazolin-7-yl]acetic acid (IQA), CX-4945 and 6,7-dichloro-1,4-dihydroxy-8-hydroxy-4-[(4-methylphenylamino)methylen]dibenzo [b,d]furan-3(2H)-one (TF).

Particularly, the CK2 inhibitor is CX-4945 (silmitasertib) having the following structure:

An immunotherapeutic agent is an agent that can modulate the physiological levels of one or more cytokines in the tumor microenvironment of cancers. In some embodiments, the immunotherapeutic agent induces local production of at least one endogenous cytokine that has cytotoxic effect on tumor cells, such as TNF-α or IFN-γ. In some embodiments, the immunotherapeutic agent inhibits the production of an endogenous cytokine that interferes with T-cell recognition and destruction of cancer cells, such as IL-10, TGFβ, or VEGF. In other embodiments, an immunotherapeutic agent is an agent that can induce tumor cell production of one or more chemokines that attract immune cells such as dendritic cells, effector T-cell (e.g., CD8+ lymphocytes), and natural killer (NK) cells to tumor cells□□In some embodiments, the chemokines include, but are not limited to, CCL19, CCL20, CCL21, CX3CL1, CXCL9, and CXCL10.

In other embodiments, an immunotherapeutic agent is an agent that induces immune checkpoint blockade, such as PD-1 blockade and CTLA-4 blockade. Immune checkpoint inhibitors are known to provide some anti-tumor activity in humans, this partial anti-tumor activity is only observed in a fraction of treated subjects. Immune checkpoint inhibitors comprise an antagonist of an inhibitory receptor which inhibits the PD-1 or CTLA-4 pathway, such as an anti-PD-1, anti-PD-L1 or anti-CTLA-4 antibody or inhibitor. Examples of PD-1 or PD-L1 inhibitors include without limitation humanized antibodies blocking human PD-1 such as lambrolizumab (anti-PD-1 Ab, trade name Keytruda) or pidilizumab (anti-PD-1 Ab), bavencio (anti-PD-L1 Ab, avelumab), imfinzi (anti-PD-L1 Ab, durvalumab), and tecentriq (anti-PD-L1 Ab, atezolizumab) as well as fully human antibodies such as nivolumab (anti-PD-1 Ab, trade name Opdivo). Other PD-1 inhibitors may include presentations of soluble PD-1 ligand including without limitation PD-L2 Fc fusion protein also known as B7-DC-Ig or AMP-244 and other PD-1 inhibitors presently under investigation and/or development for use in therapy. In addition, immune checkpoint inhibitors may include without limitation humanized or fully human antibodies blocking PD-L1 such as durvalumab and MIH1 and other PD-L1 inhibitors presently under investigation.

The active ingredients described herein can be prepared pharmaceutical compositions by methods which are commonly used, using excipients commonly used in this field, that is, pharmaceutical excipients, pharmaceutical carrier, or the like.

As a solid composition for the oral administration, a tablet, powder, a granule, and the like is used. In such solid composition, one or two or more kinds of active ingredients are mixed with at least one inert excipient. The composition may contain an inert additive, for example, a lubricant, a disintegrant, a stabilizer, a solubilizer, and the like by commonly used methods.

A liquid composition for the oral administration includes an emulsion, a solution preparation, a suspension, a syrup or an elixir, and the like which is pharmaceutically acceptable, and includes a generally used inert diluent, for example, purified water or ethanol. The liquid composition may contain adjuvants such as a solubilizing agent, a wetting agent, and a suspension, a sweetener, a flavor, an aromatic, or a preservative in addition to the inert diluent.

The injection for the parenteral administration includes a sterile aqueous or non-aqueous solution preparation, a suspension or an emulsion. As the aqueous solvent, for example, distilled water for injection or physiological saline is included. As the non-aqueous solvent, for example, alcohols such as ethanol are included. Such a composition may further include a tonicity agent, a preservative, a wetting agent, an emulsifier, a dispersant, a stabilizer, or a solubilizer. These are sterilized by, for example, filtration through a bacteria-retaining filter, mixing of a germicide, or irradiation. In addition, these can also be used in a manner in which a sterile solid composition is prepared, and is dissolved or suspended in sterile water or a sterile solvent for injection before being used.

The transmucosal agent such as a transnasal agent and the like is used in a solid, liquid, or semi-solid form, and can be prepared according to methods known in the related art. For example, a known excipient, a pH adjuster, a preservative, a surfactant, a lubricant, a stabilizer, a thickener, and the like may be suitably added. In administration, it is possible to use an appropriate device for inhalation or insufflation.

The co-administration may include simultaneous administration of an anti-cancer agent, a CK2 inhibitor and optionally an immune checkpoint inhibitor in the same or different dosage form, or separate administration of the therapeutic agents. For example, the anti-cancer agent, CK2 inhibitor and optionally immune checkpoint inhibitor may be simultaneously administered. Alternatively, the anti-cancer agent can be administered in combination with a CK2 inhibitor and optionally an immune checkpoint inhibitor, wherein the anti-cancer agent can be administered in combination with a CK2 inhibitor and optionally an immune checkpoint inhibitor are formulated for separate administration and are administered concurrently or sequentially.

While the following examples provide further detailed description of certain aspects and embodiments of the disclosure, they should be considered merely illustrative and not in any way limiting to the scope of the claims.

EXAMPLES

Example 1 CX-4945 Shows In Vivo Synergy with DNA Damaging Agent Gemcitabine

Figure 1:
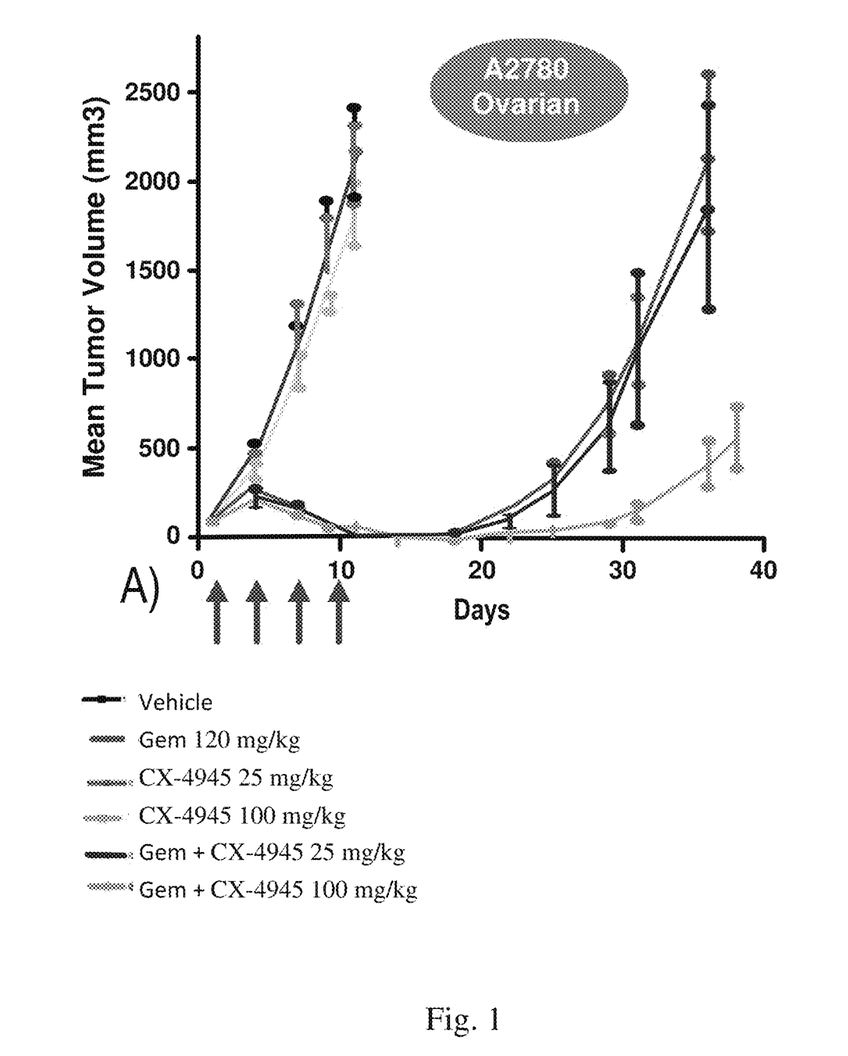
FIG. 1 shows the mean tumor volume in an ovarian tumor model.
Figure 2:
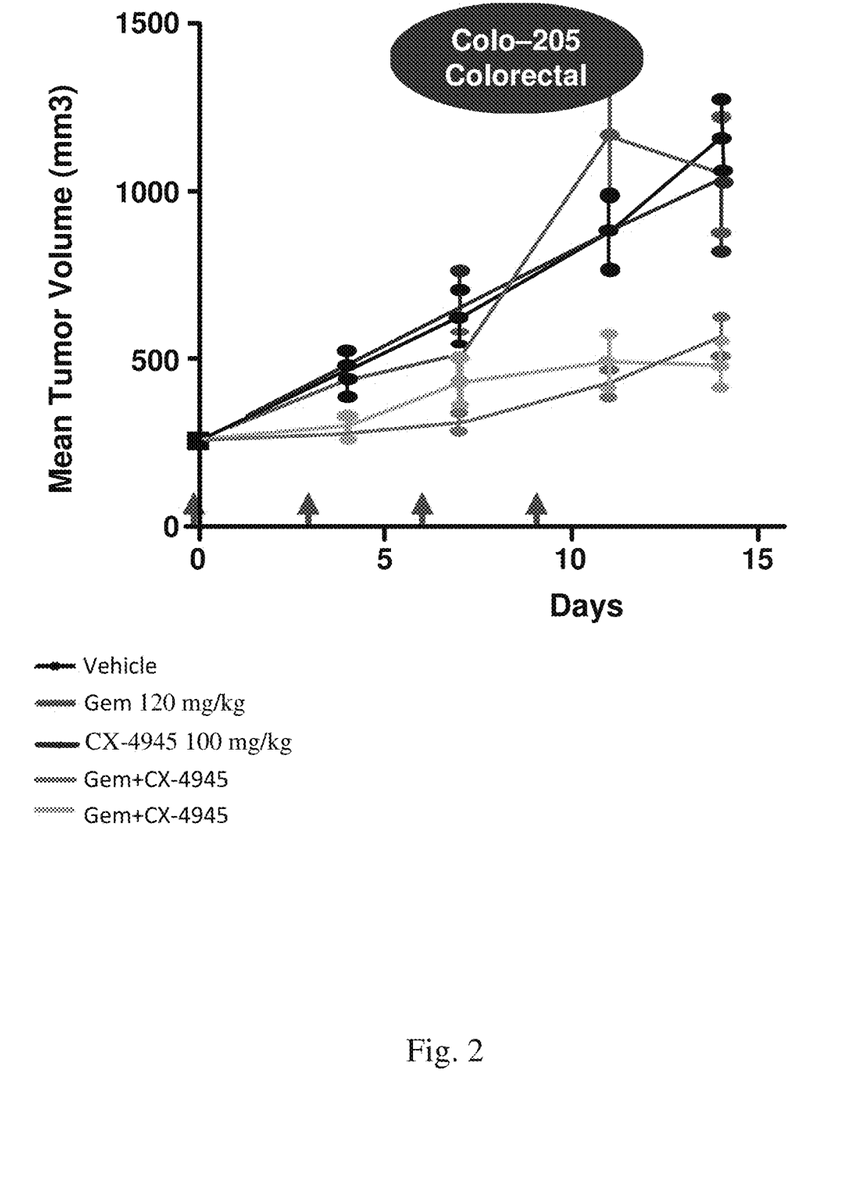
FIG. 2 shows the mean tumor volume in a colorectal cancer model.

In the A2780 ovarian tumor model, a significant increase in time to endpoint was demonstrated with a combination of gemcitabine (Gem) (120 mg/kg) and CX-4945 (25 mg/kg or 100 mg/kg) (FIG. 1), following only 4 doses, as compared to administration of each as single agent. The Colo-205 colorectal cancer model is resistant to each individual agent alone (FIG. 2). However, gemcitabine and CX-4945 in combination significantly reduce tumor growth, suggesting this combination may be effective in indications where gemcitabine alone is not approved.

Example 2 Potentiation of the Antitumor Effect by the Pharmaceutical Combination in a Cancer Animal Model Table 1 shows that the pharmaceutical combinations described in this invention produce a synergistic antineoplastic effect in vivo. Using 60 mg/kg of gemcitabine with i.v. injection and 100 mg/kg of CX-4945 orally administered to A2780 ovarian cancer xenografts was well tolerated and significantly enhanced the antitumor activity compared to gemcitabine alone. Time to endpoint (TTE) analysis showed a significant delay in time to endpoint for Gemcitabine, CX-4945 and the combination of both agents.

TABLE 1

|  | Vehicle | Gemcitabine (60 mg/kg) | CX-4945 (100 mg/kg) | Gem + CX-4945 |
|---|---|---|---|---|
| % TGI |  | 68% | 20% | 99% |
| Median TTE days | 14 | 28 | 18 | 39 (6 CR*, 2 PR**) |

*CR: complete response
**PR: partial response

Example 3 CX-4945 Significantly Increases T Cells in Tumor and Synergistically Inhibits Tumor Growth with Chemotherapeutic Agents In Vivo Efficacy studies of tumor growth inhibition and T cells activities was conducted in an immune-competent syngeneic mouse models, 4T1, that is known to be resistant to the treatment of immune checkpoint inhibitors such as anti-PD1, anti-PD-L1, and anti-CTLA4. The resistance to these antagonists that modulates T cell co-stimulatory signaling indicate a high immune suppressive tumor microenvironment.

This series of studies were conducted in Balb/C mice that are six to eight weeks old. Breast cancer cells, 4T1, were injected subcutaneously with $3 \times 10^5$ cells in 0.1 ml PBS to the right flank of the mice. Mice were randomized for treatment when the mean tumor size reached approximately 80-120 mm$^3$. Treatment were administered with CX-4945 and/or cisplatin at the doses and schedules described in Table 1. CX-4945 is formulated in 25 mM $Na_2HPO_4$ solution (pH=9.2) and administered by oral gavage. Cisplatin was dissolved in saline buffer and administered by intraperitoneal injection. Tumors were measured two dimensionally (width×length) with an electronic caliper and tumor volume was calculated with the formula $V=(L \times W \times W)/2$, where V is tumor volume, L is tumor length (the longest tumor dimension) and W is tumor width (the longest tumor dimension perpendicular to L). The mice were monitored twice weekly and euthanized when tumor sizes reached approximately 800-1000 mm$^3$ for flow cytometry analysis.

TABLE 2

Study Design and 14 day-Antitumor Activities

| Treatment | Dose Level (mg/kg) | Route of Administering | Dosing Frequency & Duration | % TGI |
|---|---|---|---|---|
| Vehicle | N/A | Oral Gavage | BID, Day 0-13 | N/A |
| CX-4945 | 75 | Oral Gavage | BID, Day 0-13 | 18% |
| Cisplatin | 6 | Intraperitoneal Injection | QW, Day 0 and 7 | 45% |

TABLE 2-continued

Study Design and 14 day-Antitumor Activities

| Treatment | Dose Level (mg/kg) | Route of Administering | Dosing Frequency & Duration | % TGI |
|---|---|---|---|---|
| CX-4945 | 75 | Oral Gavage | BID, Day 0-13 | 60% |
| Cisplatin | 6 | Intraperitoneal Injection | QW, Day 0 and 7 | |

Figure 3:
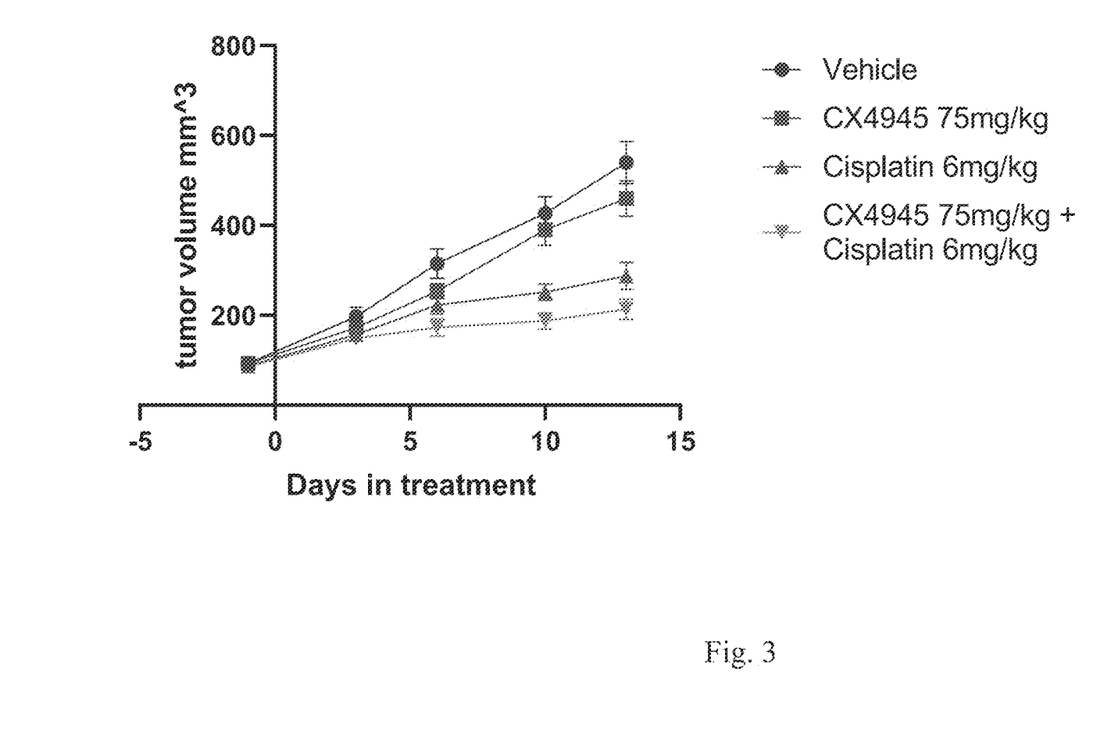
FIG. 3 shows the 14 day anti-tumor growth activities of CX-4945 with Cisplatin treatment in immune-competent syngeneic mice model, 4T1.

Anti-tumor activities were measured as % Tumor Growth Inhibition (% TGI) at the time of euthanized. TGI was calculated as % TGI=100×(1−T/C). T and C were the mean tumor volume of the treated and control groups, respectively, on the given day. The 14-day anti-tumor activity is shown in Table 2 and the tumor growth curve is shown in FIG. 3. In summary, CX-4945 show synergistic effect in anti-tumor growth inhibition with a platinum-based DNA damage agent, cisplatin.

The composition of immune cells was analyzed with multi-color flow cytometry (FACS) at days when tumor reaches 800-1000 mm$^3$. Tumors were treated with dissociation media (Miltenyi, CAT #130-096-730) and resuspend in FACS buffer. T cell infiltration was measured by the investigating the number of T cells in the tumor samples. CD4 T, CD8 T, activated CD4 T, and activated CD8 T cells were identified by cell surface marker as CD45$^+$CD3$^+$CD4$^+$, CD45$^+$CD3$^+$CD8$^+$, CD45$^+$CD3$^+$CD4$^+$CD69$^+$, and CD45$^+$CD3$^+$CD8$^+$CD69$^+$, respectively. The absolute count of cells was measured by normalized number of cells with counting beads (eBiosciences CAT #01-1234-42) and the weight of each tumor sample. Absolute count of tumor-infiltrating T cells was calculated by the formula as Absolute count (cells/mg)=[(cell count×eBead Volume)/(eBead count×tumor weight)]×eBead concentration.

Figure 4:
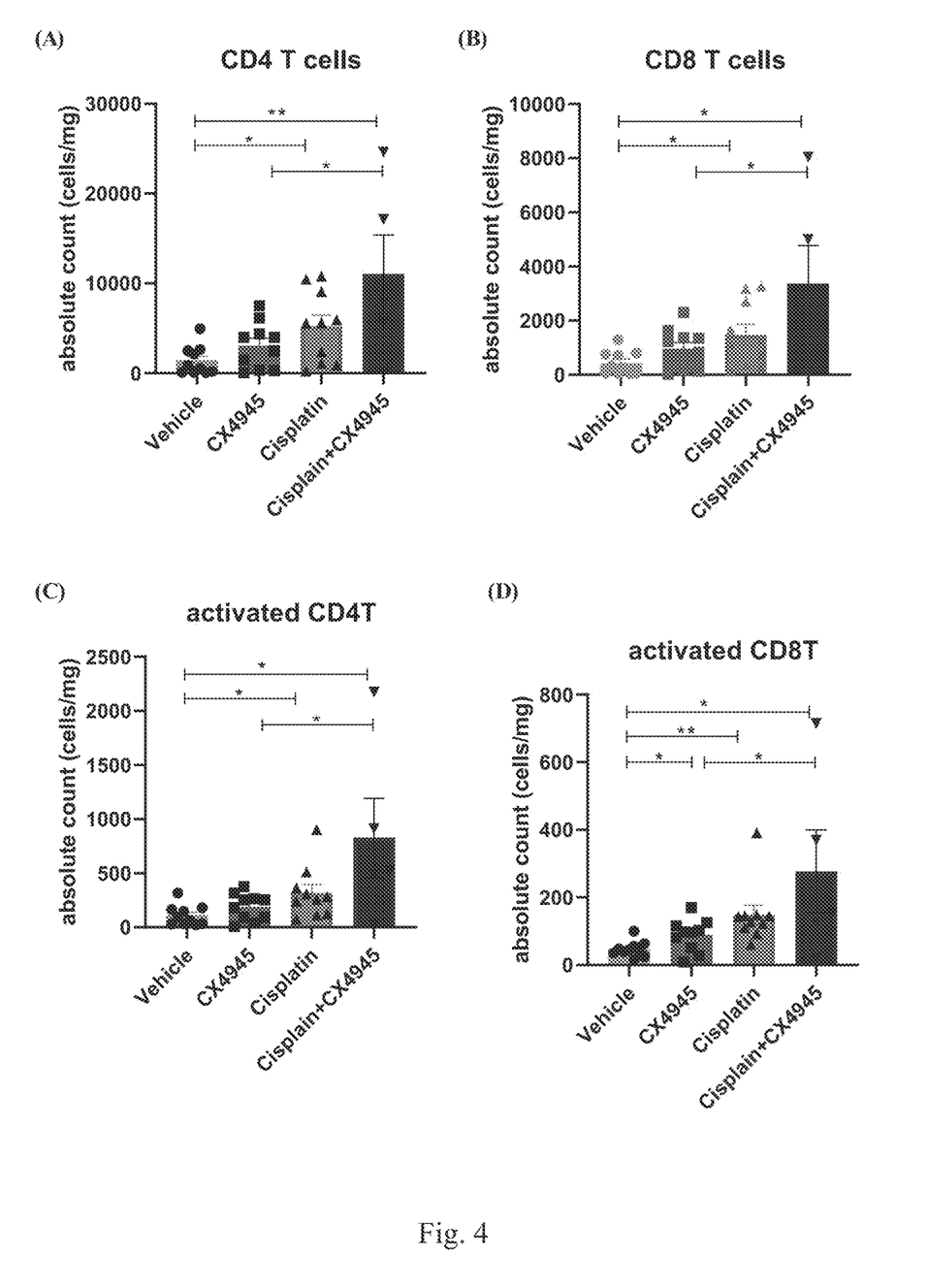
FIG. 4 shows the tumor-infiltrating CD4 and CD8 T cells after treatment of CX-4945 and/or cisplatin in syngeneic mouse model 4T1.

Treating immune competent mice with CX-4945 does not decrease number of MDSC systemically or locally in the tumor microenvironment. Additionally, treating immune competent mice with CX-4945 and cisplatin unexpectedly increase both CD4 and CD8 T cells in the tumor microenvironment. Particularly, the combination of CX-4945 and cisplatin presented synergistic effect in increasing number of T cells and activated T cells in the tumor microenvironment (FIG. 4).

The tumor growth inhibition of the combination of CX-4945 and Cisplatin was associated with the cytotoxic T cell activities in the tumor microenvironment. Depleting CD8 T cells by administering anti-CD8 antibodies along with the treatment demolished the anti-tumor growth activities.

Figure 5:
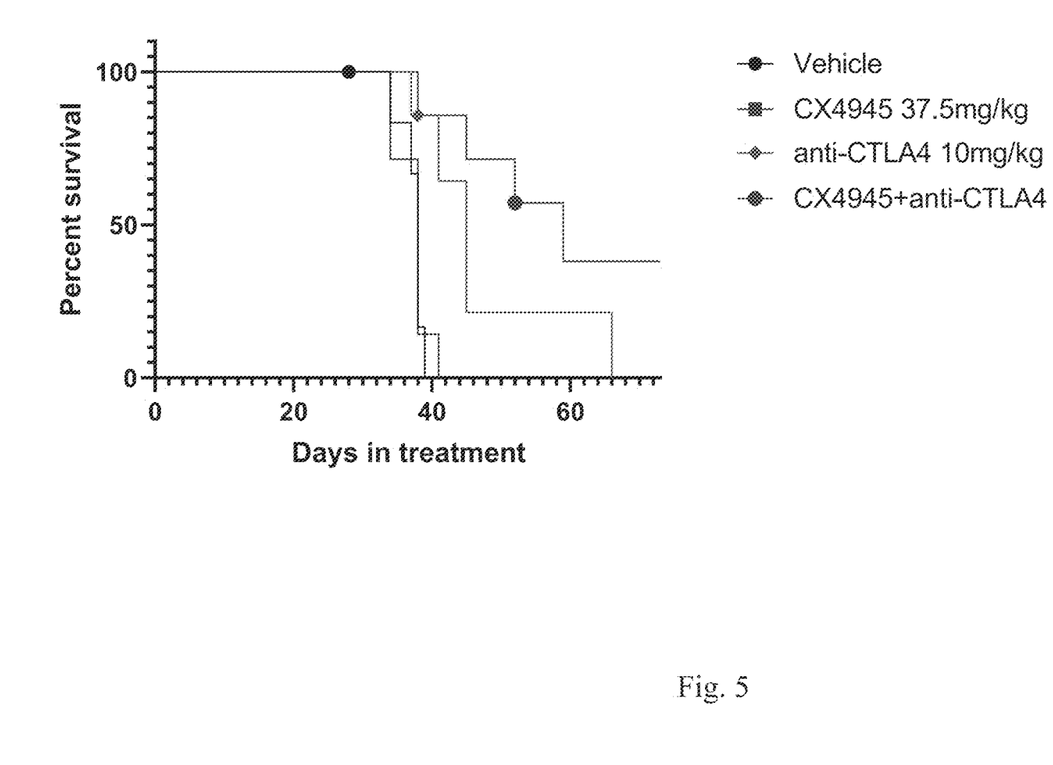
FIG. 5 shows the Kaplan-Meier survival curve of subjects treated with vehicle, 37.5 mg/kg of CX-4945, 10 mg/kg of anti-CTLA4, and the combination of CX-4945 and anti-CTLA-4.

Example 4 Combination of CX-4945 with Anti-CTLA4 Significantly Increases the Likelihood of Survival in a Subject with Cancer The capability of CX-4945 in enhancing T cell activities in effectively tumor killing was also tested in the same syngeneic model, 4T1, which has demonstrated refractory to anti-PD1 or anti-CTLA4 treatment. This series of studies were conducted in Balb/C mice that are six to eight weeks old. Breast cancer cells, 4T1, were injected subcutaneously with 3×10$^5$ cells in 0.1 ml PBS to the right flank of the mice. Mice were randomized when the mean tumor size reached approximately 80-120 mm$^3$ for treatment. Mice were then treated with 37.5 mg/kg of CX-4945 via oral gavage, and/or 10 mg/kg of anti-CTLA4 antibody via intra-peritoneal injection. Kaplan-Meier survival curves were generated and Log Rank test was performed. Mice with 3000 mm$^3$ tumor growth were considered reaching tumor growth endpoint. Combination of CX-4945 and anti-CTLA4 significantly improved overall survival of tumor-bearing mice (FIG. 5), and 28.5% of the group treated with such combination reached complete remission.

Figure 6:
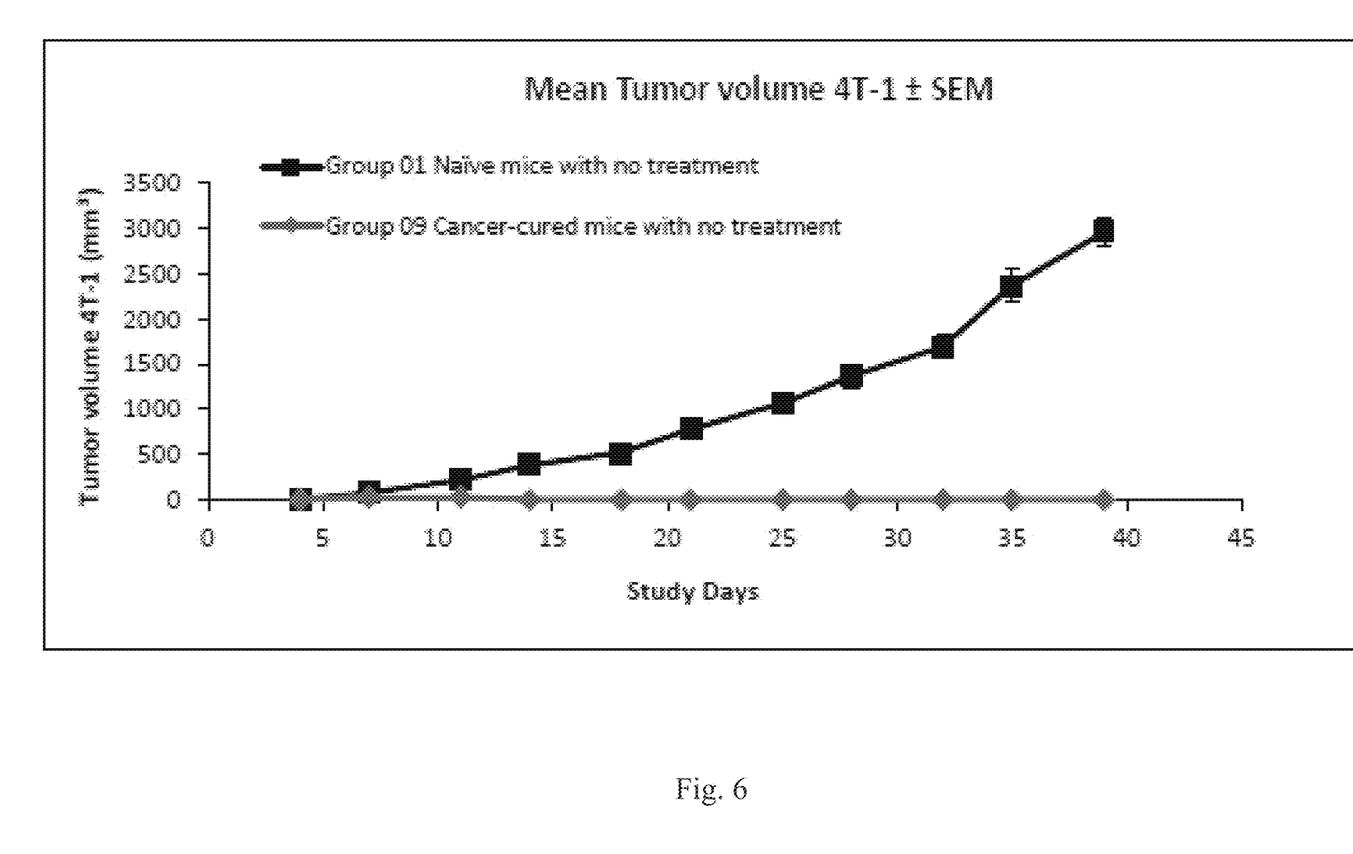
FIG. 6 shows the tumor growth curves (mean tumor volume over time) of the naïve mice group and the Cancer-cured mice group.
Figure 7:
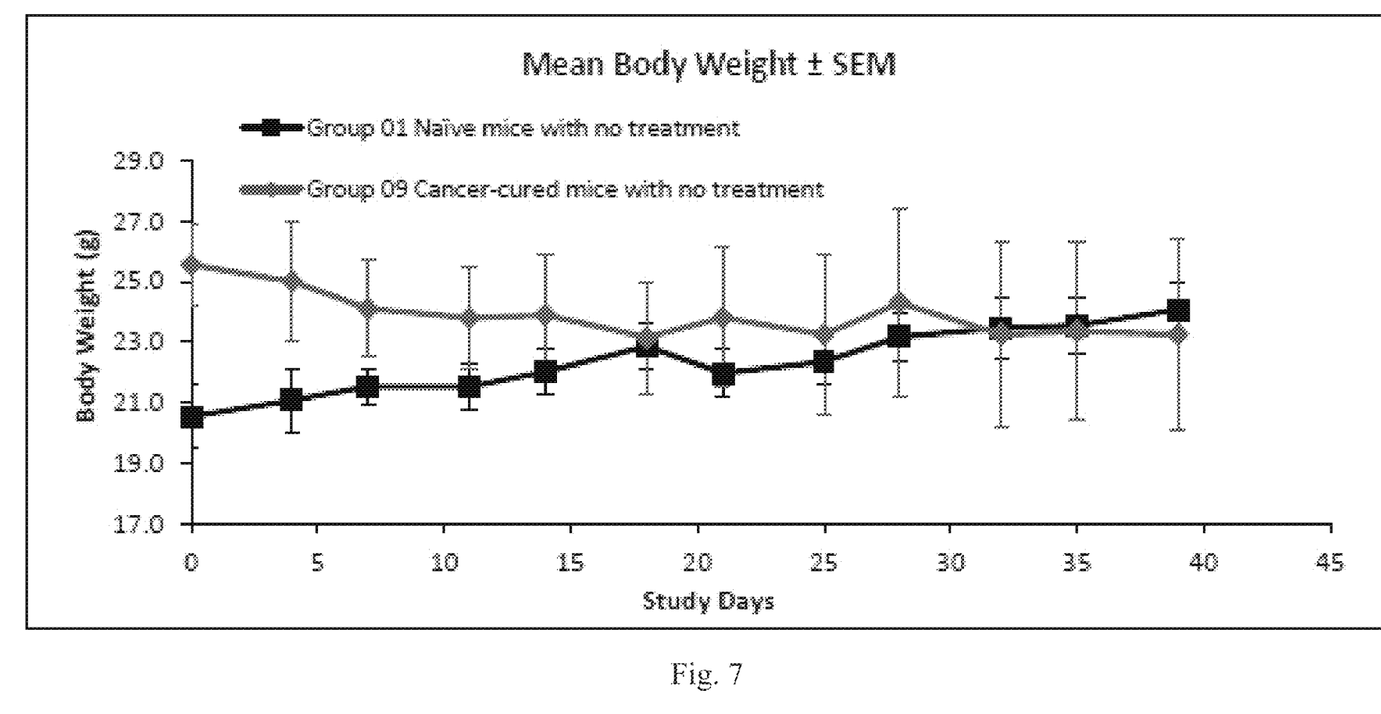
FIG. 7 shows the results of mean body weight changes in the tumor bearing mice.

The survived mice (i.e., the cancer-cured mice) (tumor complete regression) generated in the efficacy phase (4T-1) was re-challenged with the same cancer cell line-4T-1 to see if the mice could develop immunity to the same cancer cell line. After tumor cell inoculation, the mice (naïve mice and cancer-cured mice) were checked daily for morbidity and mortality. At the time of routine monitoring, the animals were checked for any effects of tumor growth and treatments on behavior such as mobility, food and water consumption, body weight gain/loss (body weight was measured twice per week), and any other abnormalities. Mortality and observed clinical signs were recorded for individual animals. The tumor growth curves (mean tumor volume over time) of different groups were shown in FIG. 6. The results of mean body weight changes in the tumor bearing mice were shown in FIG. 7. The results shown that 4T-1 tumor cannot developed in the cancer-cured mice from initial treatment with CX4945 and anti-mouse CTLA-4 antibody after re-challenge, which suggested the acquired immunity after the drugs treatments. In conclusion, the survived mice treated with the combination of CX-4945 and anti-CTLA4 antibody displayed superior activities in tumor growth inhibition when re-challenged with the 4T1 tumor cells, indicating immune memory being successfully induced.

In summary, activated T cell activities in the tumor microenvironment and immune memory induced by the combinational CX-4945 regimens contribute to a prolonged survival of subjects with tumors.

Example 5 Comparison of Clinical Trial Results

ABC-02 trial collected data of 208 patients, of which 138 patients received first line chemotherapy with gemcitabine and cisplatin (Juan Valle et al., N. Engl. J. Med. 362:1273-1281 (2010)). See Table 3 below.

TABLE 3

| Patients | Identified | Overall Survival (OS) post disease progression |
|---|---|---|
| Group I (n = 76) | Chemotherapy, meet the criteria | 3.6 months |
| Group II (n = 62) | Chemotherapy, not meet the criteria | 4.4 months |

In comparison, the results of a Phase I/II study of CX-4945 in Combination with gemcitabine and cisplatin in the frontline treatment of patients with cholangiocarcinoma are given in Table 4 below.

TABLE 4

| Patient ID | On treatment period | Overall Survival (OS) post disease progression |
|---|---|---|
| Pt. 1 | 11 months | 11 months |
| Pt. 2 | 2 months | 10 months |

Example 6 Treatment with the Combination of CX-4945 with Cisplatin and Gemcitabine Increases the Overall Survival of Subjects with Cholangiocarcinoma In a phase I, open-label, multicenter, multidose, dose-escalation, study of CX-4945 in combination with gemcitabine and cisplatin in cholangiocarcinoma patients, 50 patients with unresectable cholangiocarcinoma were administered CX-4945 in conjunction with gemcitabine plus cisplatin given in 21-day cycles. CX-4945 was administered orally twice daily on Days 0, 1, and 2, and on Day 7, 8, and 9, around the administration of intravenous cisplatin 25 mg/m$^2$ and gemcitabine 1,000 mg/m$^2$ on Days 1 and 8. Treatment repeated every 21 days in the absence of disease progression or unacceptable toxicity.

Figure 8:
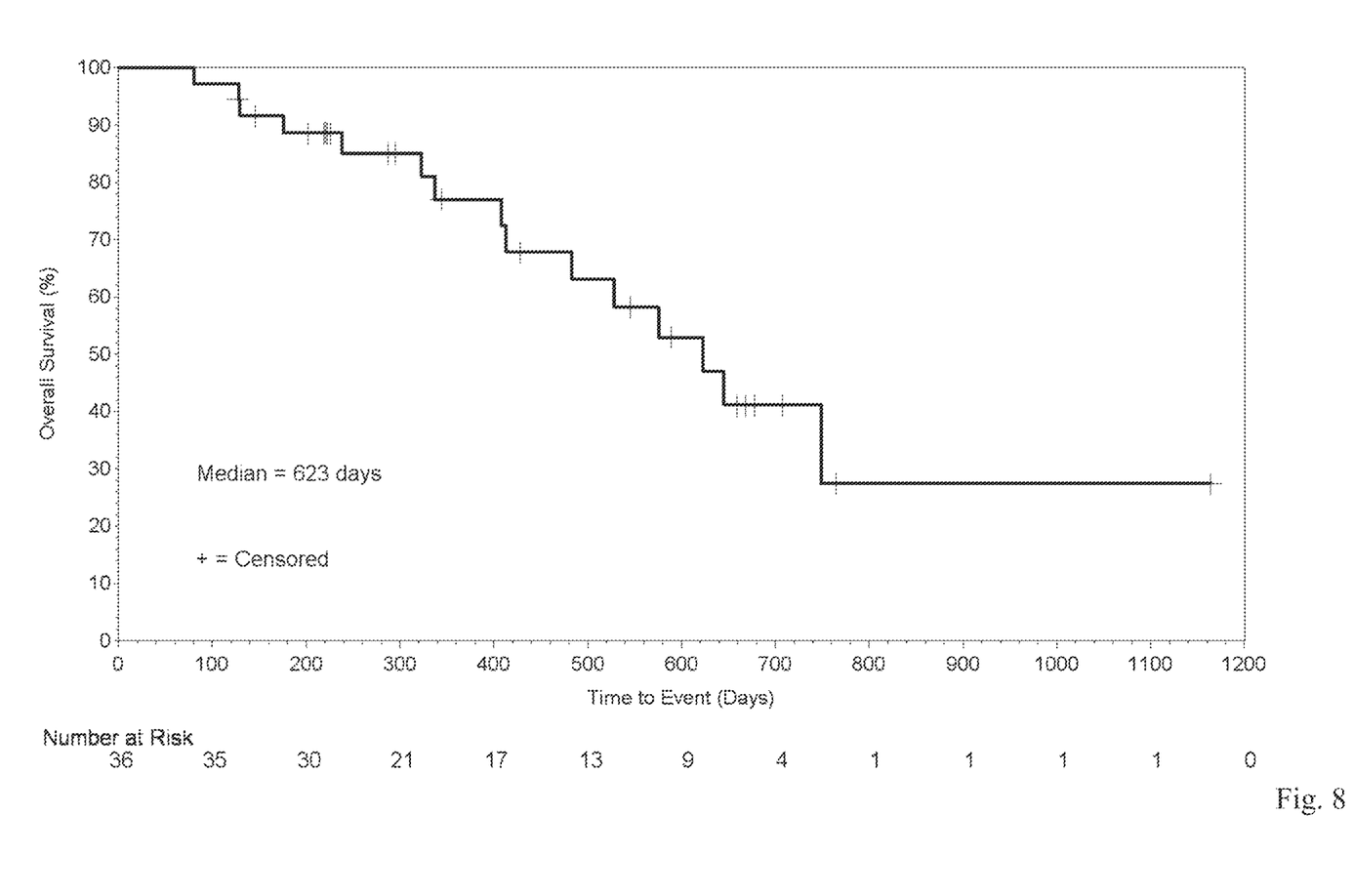
FIG. 8 shows the Kaplan-Meier survival curve of subjects in a phase 1 clinical trial, in which the patients received at least one cycle of CX-4945 in conjunction with cisplatin and gemcitabine without dose modification or dose reduction.

Of the 50 patients, 36 patients received at least one cycle of study drug without dose modification or dose reduction and were designated as a modified intension to treat (mITT) population. Overall survival of mITT population in this study was compared to study ABC-02, an extended phase 3 randomized control trial in patients with unresectable, recurrent, or metastatic biliary tract carcinoma (intrahepatic or extrahepatic cholangiocarcinoma, gallbladder cancer, or ampullary carcinoma). The median overall survival of the mITT population was 20.8 months (95% CI: 13.8-NE) while the median overall survival of ABC-02 study was 11.7 months (95% CI: 9.5-14.3), indicating an increasing likelihood of survival of cholangiocarcinoma patients treated with CX-4945 in combination of cisplatin and gemcitabine. The Kaplan-Meier survival curve of the mITT population is shown in FIG. 8.

What is claimed is:

1. A pharmaceutical combination comprising a therapeutically effective amount of CX-4945:

or a pharmaceutically acceptable salt or ester thereof; and
at least one anti-CTLA4 antibody.

2. A method for treating a cancer and/or inhibiting cancer metastasis, recurrence or progression in a subject or increasing the likelihood of survival over a relevant period in a subject diagnosed with a cancer, comprising administering to the subject a combination of an immune checkpoint inhibitor and a CK2 inhibitor, wherein:
the immune checkpoint inhibitor is an anti-CTLA4 antibody, and
the CK2 inhibitor is CX-4945 having the following structure, or a pharmaceutically acceptable salt or ester thereof:

3. The method of claim 2, wherein the administration increases tumor-specific T cells in the tumor microenvironment in a subject.

4. The method of claim 2, wherein the combination results in immunological memory to said cancer.

5. The method of claim 2, wherein the method comprises at least one administration cycle, wherein the cycle is a period of eight weeks or less.

6. The method of claim 5, wherein the cycle is a period of four weeks.

7. The method of claim 5, wherein the CK2 inhibitor is administered in a daily dose in the range from about 25 mg per kg of subject weight (about 25 mg/kg) to about 2000 mg/kg.

8. The method of claim 7, wherein the daily dose is in the range of about 50 mg/kg to about 200 mg/kg, and the CK2 inhibitor is administered twice a day.

9. The method of claim 2, wherein the immune checkpoint inhibitor and the CK2 inhibitor are in synergistically effective amounts.

10. The method of claim 2, wherein the immune checkpoint inhibitor is administered in a dose in the range from about 1 mg per kg of subject weight (about 1 mg/kg) to about 20 mg/kg.

11. The method of claim 2, wherein the dose of the immune checkpoint inhibitor is in the range of about 8 mg/kg to about 15 mg/kg.

12. The method of claim 2, wherein the immune checkpoint inhibitor is ticilimumab or ipilimumab.

13. The method of claim 2, wherein the cancer is glioblastoma, skin cancer, liver cancer, colorectal carcinoma, glioblastoma, gastric cancer, colorectal cancer, esophageal cancer, lung cancer, pancreatic cancer, renal cell carcinoma, benign prostate hyperplasia, prostate cancer, ovarian cancer, melanoma, breast cancer, chronic lymphocytic leukemia (CLL), Merkel cell carcinoma, Non-Hodgkin lymphoma, acute myeloid leukemia (AML), gallbladder cancer, cholangiocarcinoma, urinary bladder cancer, or uterine cancer.

14. The method of claim 13, wherein the cancer is breast cancer, colorectal carcinoma or colorectal cancer.

* * * * *